United States Patent [19]

Danzig et al.

[11] Patent Number: 4,799,953

[45] Date of Patent: Jan. 24, 1989

[54] METHOD FOR REGULATING PLANT GROWTH USING SULFUR-CONTAINING ORGANIC ACIDS

[75] Inventors: Morris J. Danzig, Northbrook; Alan M. Kinnersley, Bedford Park, both of Ill.

[73] Assignee: CPC International Inc., Englewood Cliffs, N.J.

[21] Appl. No.: 105,937

[22] Filed: Oct. 8, 1987

[51] Int. Cl.$^4$ .................... A01N 31/00; A01N 37/00; C07C 153/09; C07C 53/00
[52] U.S. Cl. .................................. 71/98; 558/255; 71/100; 562/512; 562/594
[58] Field of Search ............... 558/255; 71/100, 98; 562/512, 594

[56] References Cited

U.S. PATENT DOCUMENTS 3,148,049  9/1964  Herschler .................. 562/512
4,297,282  10/1981  Ohashi et al. ............... 558/255

FOREIGN PATENT DOCUMENTS 1916054  10/1970  Fed. Rep. of Germany ...... 562/512

OTHER PUBLICATIONS

Mikami, et al., *Agr. Biol. Chem.*, 34, pp. 977–979, (1970).

Primary Examiner—Mary C. Lee
Assistant Examiner—Robert C. Whittenbaugh

[57] ABSTRACT

This invention relates to condensation polymers of thiolactic and thioglycolic acids. These polymers, as well as thiolactic acid, 2,2'-dithiobisacetic acid, and 2,2'-dithiobispropanoic acid, increase both the rate of plant growth and the concentration of chlorophyll in the plant.

8 Claims, No Drawings

METHOD FOR REGULATING PLANT GROWTH USING SULFUR-CONTAINING ORGANIC ACIDS

FIELD OF THE INVENTION

The present invention relates to polymers of thioglycolic and thiolactic acids useful in a process for increasing the rate of plant growth and the chlorophyll concentration in plants. In this process, plants are treated with dilute solutions of these polymers or certain other sulfur-containing organic acids.

BACKGROUND OF THE INVENTION

Various derivatives of organic acids have been proposed as plant growth regulators. For example, West German Patent 19 16 054 discloses the use of alpha-hydroxy- or alpha-ketoalkanoic acids, having 7 to 10 carbon atoms, and their derivatives, particularly amides, for promoting the growth of plants under drought conditions. U.S. Pat. No. 3,148,049 discloses certain halogenated keto acids, such as halogenated acetoacetic acid, as plant growth regulators. U.S. Pat. No. 3,351,653 discloses the use of fluorinated hydroxy acids and esters as herbicides. In 1970, Mikami, et al, *Agr. Biol. Chem.*, 34, 977–979, reported test results of a number of hydroxy acids as plant growth regulators. Several of these, particularly, certain aromatic hydroxy acids, were shown to be root growth promoters. However, some of the simple acids, such as glycolic acid, caused suppression of root growth rather than root growth promotion. None of the hydroxy acids revealed any activity in the straight growth-promotion test used.

We have now discovered, to our surprise, that certain sulfur-containing organic acids do act as growth promoters and can increase chlorophyll concentration when applied to growing plants.

SUMMARY OF THE INVENTION

In accordance with this invention, there is provided a compound represented by the formula

where n is a small whole number from 1 to 10 and the Rs are the same or different and denote H or CH$_3$.

Further provided in accordance with this invention, is a process for increasing the rate of growth of a plant which comprises supplying to the plant an effective amount of one or more sulfur-containing acids selected from the group consisting of thiolactic acid, 2,2'-dithiobisacetic acid, 2,2'-dithiobispropanoic acid, and a compound represented by Formula I, where n is a small whole number from 1 to 10 and the Rs are the same or different and denote H or CH$_3$.

Also provided, in accordance with this invention, is a process for increasing the concentration of chlorophyll in a plant which comprises supplying to the plant an effective amount of one or more sulfur-containing acids selected from the group consisting of thiolactic acid, 2,2'-dithiobisacetic acid, 2,2'-dithiobispropanoic acid, and a compound represented by Formula I, where n is a small whole number from 1 to 10 and the Rs are the same or different and denote H or CH$_3$.

DETAILED DESCRIPTION OF THE INVENTION

The acids generally useful in the practice of this invention are certain sulfur-containing organic acids and condensation polymers obtained by condensing two or more molecules of certain thiol acids by the elimination of water. Mixed polymers of two different thiol acids may also be used. Exemplary acids used in the practice of this invention as noted above include thiolactic acid and the dithioacids: 2,2'-dithiobisacetic acid and 2,2'-dithiobispropanoic acid. Also useful in the practice of this invention are polymers of thiolactic acid, polymers of thioglycolic acid, copolymers of thioglycolic and thiolactic acids. These polymers are represented by the formula

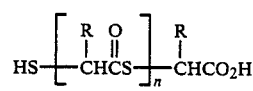

where n is a small whole number from 1 to 10 and the Rs are the same or different and denote H or CH$_3$.

The activity of the acids used in the practice of this invention was discovered when they were tested in the duckweed promotion assay of Mitchell and Livingston, *Methods of Studying Plant Hormones and Growth-Regulating Substances*, USDA-ARS Agriculture Handbook, 336, pp. 66–67 (1968). This test showed that various sulfur-containing organic acids have growth-promoting abilities when used in the concentration of between about 5 and about 500 ppm (parts per million) on a weight/volume basis. Polymers of thioglycolic acid and thiolactic acid have shown good growth-promoting ability when used at a concentration of 10 ppm. In the case of polythiolactic acid, concentrations of 100 ppm proved to be somewhat growth inhibitory but they led to enhanced chlorophyll concentration in the plants. On the other hand, the dithiobis acids showed almost constant growth-promoting ability when used in concentrations from 10 ppm to 200 ppm.

An additional benefit derived from growing plants in the presence of the sulfur-containing acids of this invention is that the plants accumulate more chlorophyll. The presence of such acids in the growth medium, particularly at concentrations of from about 10 ppm to about 200 ppm on a weight/volume basis, greatly enhances the amount of chlorophyll accumulated per milligram of plant weight.

As noted above, the activity of the acids used in the practice of this invention was discovered when they were tested in the duckweed promotion assay. Since his assay involves growing the plants on an aqueous solution, it demonstrates the usefulness of the process in promoting the growth of plants in hydroponic culture. Likewise, the process of this invention is useful when plants are propagated by means of tissue culture. This is a particularly useful application of these acids, since many plants are now propagated commercially by means of tissue culture.

The acids used in the process of the present invention are seen to produce more than one growth-regulating effect on the plants. The particular growth-regulating effect produced by a plant depends, of course, on a number of variables, including the acid or mixture of acids used, the concentration and total amounts of the acids used, the time at which the acids are applied, and the type of plant species which is treated. The amount of material added is the effective amount needed to obtain the response desired. In general, the acids are utilized in dilute aqueous solutions which contain the acids in concentrations of from about 5 to about 500 ppm on a weight/volume basis. For most applications, the preferred concentrations are from about 10 ppm to about 100 ppm. The most suitable concentrations for a particular application are readily determined by well-known screening tests, such as those given in the examples.

Solutions of the acids are conveniently applied to the plants in the water added for plant growth. This water may also contain nutrients required by the plants. Optionally, solutions of the acids may be sprayed onto or otherwise applied to the roots, stems, or leaves of the plants.

The following specific examples illustrate the present invention. They are not intended to limit the invention in any way. When concentrations are given in ppm, they are on a weight/volume basis. The thiolactic acid used in the examples was obtained from the Aldrich Chemical Company, Milwaukee, Wis. It was converted into polythiolactic acid by heating 10.6 parts of the acid with 1 part of strong acid cation-exchange resin under reduced pressure for 72 hours at 105°–110° C. The resin was removed by filtration and unreacted thiolactic acid was removed by distillation under high vacuum. Polythioglycolic acid was prepared from thioglycolic acid using the same process as was used to prepare polythiolactic acid. The copolymer of thiolactic and thioglycolic acids was prepared in a similar manner by heating equimolar amounts of the starting acids in the presence of the strong acid ion-exchange resin. The presence of the

linkage in these polymers was shown by $C^{13}$ NMR analysis.

The 2,2'-dithiobispropanoic acid was obtained by the slow addition of 2.5 ml of 30% hydrogen peroxide to a solution of 10.6 g of thiolactic acid in 15 ml of acetone at 5° C. The mixture was held at 5° C. for 24 hours and then left at room temperature for 48 hours. The solvent was removed under reduced pressure and the residue was dissolved in chloroform. The chloroform solution was washed with water and dried before the solvent was removed under reduced pressure to give a residual syrup that was used in the experiments.

2,2'-dithiobisacetic acid was prepared in a like manner by the hydrogen peroxide oxidation of thioglycolic acid.

EXAMPLE 1

Duckwee (*Lemna minor L.*) was grown following the general procedure of Mitchell and Livingston, *Methods of Studying Plant Hormones and Growth Regulating Substances*, USDA-ARS Agriculture Handbook, 336, pp. 66–67 (1968). Plants were grown on Nickell's medium as described in the handbook with the iron being present as the ferrous ion chelated with EDTA. One plant at the three-frond stage was placed in each flask. Flasks were incubated at 25° C. for 16–18 days under 300- to 500-foot candles of light for 16 hours per day. The plants were harvested and dried before plant weight was measured. All reported values represent 3 to 5 replicates.

Experiments were performed in which various concentrations of the sulfur-containing acids were added to the duckweed growth medium. A control was run in which no acid was added. The results given in Table I demonstrate that growth is greatly enhanced when comparatively small concentrations of the acids are present in the medium.

TABLE I

| DUCKWEED GROWTH ASSAY | | | | | |
|---|---|---|---|---|---|
| | Dry Weight (mg) Acid (ppm) | | | | |
| | 0 (Control) | 1 | 10 | 100 | 200 |
| Thiolactic Acid | 37 ± 6 | 43 ± 3 | 65 ± 22 | 59 ± 11 | |
| Polythiolactic Acid | 37 ± 6 | 42 ± 8 | 56 ± 6 | 22 ± 6 | |
| Polythioglycolic Acid | 49 ± 3 | 38 ± 6 | 62 ± 9 | | |
| Copolymer of Thioglycolic and Thiolactic Acids | 49 ± 3 | 47 ± 4 | 63 ± 4 | | |
| 2,2'-Dithiobisacetic Acid | 35 ± 3 | 36 ± 6 | 55 ± 7 | 62 ± 6 | 59 ± 9 |
| 2,2-Dithiobispropanoic Acid | 35 ± 3 | 36 ± 4 | 49 ± 3 | 54 ± 7 | 56 ± 4 |

EXAMPLE 2

The general procedure of Example 1 was followed and the chlorophyll content of the harvested plants was determined by the method of Kirk, *Planta*, 78, 200–207 (1968). Samples of preweighed dried duckweed were suspended in 80% acetone. The mixture was homogenized for 30 seconds using a POLYTRON® Brand Homogenizer (Brinkman Instruments, Westbury, N.Y. The mixture was centrifuged and absorption of the supernatant was read at 663 and 645 nm. From these readings, the number of micrograms of chlorophyll per milligram of dry weight was determined using the nomogram of Kirk. The results given in Tabl II show that the sulfur-containing organic acids used in the process of this invention increase the chlorphyll content of plants. This is particularly evident when the acids are present in the growth medium at concentrations of 100 ppm and higher.

TABLE II

| DUCKWEED CHLOROPHYLL CONCENTRATION ASSAY | | | | | |
|---|---|---|---|---|---|
| | Chlorophyll (μg/mg) Acid Concentration (ppm) | | | | |
| Acid | 0 (Control) | 1 | 10 | 100 | 200 |
| Polythiolactic Acid | 2.2 | | | 6.9 | |
| Polythioglycolic Acid | 1.9 | | 3.0 | | |
| Copolymer of Thioglycolic and Thiolactic Acids | 1.9 | | 3.6 | | |
| 2,2'-Dithiobisacetic Acid | 1.9 | | 4.5 | 4.7 | 4.6 |
| 2,2'Dithiobispropanoic Acid | 1.9 | | | 4.6 | 6.4 |

Thus, it is apparent that there has been provided, in accordance with the invention, an improved process for increasing the rate of plant growth and for increasing the chlorophyll content of plants which fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A compound represented by the formula

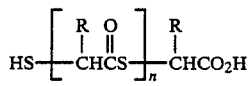

where n is a small whole number from 1 to 10 and the Rs are the same or different and denote H or CH$_3$.

2. A method for increasing the rate of growth of a plant which comprises supplying to the plant an effective amount of one or more sulfur-containing acids selected from the group consisting of thiolactic acid, 2,2'-dithiobisacetic acid, 2,2'-dithiobispropanoic acid, and a compound represented by the formula

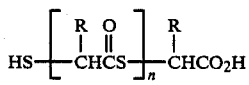

where n is a small whole number from 1 to 10 and the Rs are the same or different and denote H or CH$_3$.

3. The method of claim 2 wherein the acid is supplied to the plant in an aqueous solution at a concentration of between about 5 and about 500 parts per million on a weight/volume basis.

4. The method of claim 3 wherein the plant is *Lemna minor L.*

5. The method of claim 2 wherein the plant is grown in hydroponic or tissue culture.

6. A method for increasing the concentration of chlorophyll in a plant which comprises supplying to the plant an effective amount of one or more sulfur-containing acids selected from the group consisting of thiolactic acid, 2,2'-dithiobisacetic acid, 2,2'-dithiobispropanoic acid, and a compound represented by the formula

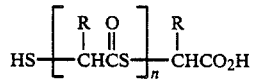

where n is a small whole number from 1 to 10 and the Rs are the same or different and denote H or CH$_3$.

7. The method of claim 6 wherein the acid is supplied to the plant in an aqueous solution at a concentration of between about 5 and about 500 parts per million on a weight/volume basis.

8. The method of claim 7 wherein the plant is *Lemna minor L.*

* * * * *